United States Patent
Willsie

(10) Patent No.: US 8,357,093 B2
(45) Date of Patent: Jan. 22, 2013

(54) MEDICAL DIAGNOSTIC IMAGING WITH REAL-TIME SCAN CONVERSION

(75) Inventor: Todd D. Willsie, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1073 days.

(21) Appl. No.: 11/897,419

(22) Filed: Aug. 29, 2007

(65) Prior Publication Data

US 2009/0062643 A1 Mar. 5, 2009

(51) Int. Cl.
*A61B 8/00* (2006.01)

(52) U.S. Cl. .......................... 600/437; 600/407; 382/128

(58) Field of Classification Search ................. 600/437, 600/407; 382/165, 168, 128, 170–171; 128/916
See application file for complete search history.

(56) References Cited

U.S. PATENT DOCUMENTS

| | | | |
|---|---|---|---|
| 3,893,075 A * | 7/1975 | Orban et al. | 345/443 |
| 5,573,001 A | 11/1996 | Petrofsky et al. | |
| 5,623,930 A * | 4/1997 | Wright et al. | 600/456 |
| 6,280,387 B1 * | 8/2001 | Deforge et al. | 600/454 |
| 6,569,101 B2 * | 5/2003 | Quistgaard et al. | 600/459 |
| 6,592,521 B1 * | 7/2003 | Urbano et al. | 600/441 |
| 2002/0047658 A1 * | 4/2002 | Nakanishi et al. | 315/364 |
| 2004/0002652 A1 | 1/2004 | Phelps et al. | |
| 2006/0145962 A1 * | 7/2006 | Jeon | 345/76 |

OTHER PUBLICATIONS

U.S. Appl. No. 11/827,679, filed Jul. 12, 2007.

* cited by examiner

*Primary Examiner* — Tse Chen
*Assistant Examiner* — Joel F Brutus

(57) ABSTRACT

Display or pixel values are scan converted from ultrasound data on the fly. As each pixel is to receive display values, the display value is determined. Scan conversion is performed sequentially, with each new value being determined in synchronization with reading display values out to the display. Rather than storage in a raster buffer, scan converted display values are output to the display while other display values for a same image are being converted.

7 Claims, 4 Drawing Sheets

MEDICAL DIAGNOSTIC IMAGING WITH REAL-TIME SCAN CONVERSION

BACKGROUND

The present invention relates to medical imaging. In particular, a system and method of scan conversion is provided.

In medical diagnostic ultrasound imaging, a patient is scanned in a linear, sector, or Vector® format. In response to the scan, ultrasound data is acquired in a polar coordinate format. The ultrasound data is used to generate an image on a display. The display format has a Cartesian coordinate format. The ultrasound data is converted from polar or Cartesian acoustic coordinate to the Cartesian display coordinate format. The ultrasound data is also converted from intensity or estimate information into red, green, blue or other video signal for display.

The display values resulting from scan conversion are output to a raster buffer. Display values for an entire image are stored in the buffer before reading out to the display. Graphics information, such as text and borders, are added to the data in the buffer. The graphics information or overlay is provided from a different video source.

Storage in the buffer introduces a time delay between scanning and display. The time delay may be reduced by providing two buffers. Display values for one image are read into one buffer while display values for a different image are read out of the other buffer. The buffers are used in a ping-pong fashion between reading in and reading out display values. However, there is still latency introduced by reading in or out all the display values for an image. The single or double buffer also uses space, increases cost, and increases power usage.

BRIEF SUMMARY

By way of introduction, the preferred embodiments described below include systems, methods, computer readable media, and instructions for scan converting in medical imaging. Display or pixel values are scan converted from ultrasound data on the fly. As each pixel is to receive display values, the display value is determined. Scan conversion is performed sequentially, with each new value being determined in synchronization with reading display values out to the display. Rather than storage of an entire image in a raster buffer, scan converted display values are output to the display while other display values for a same image are being converted.

According to a first aspect, a method of scan conversion is provided in medical diagnostic ultrasound imaging. Pixel values are sequentially output to a display. The pixel values are scan converted for the output. Each pixel value is scan converted and output prior to completing scan converting of a subsequent pixel value for a same image.

In a second aspect, a system is provided for scan conversion in medical diagnostic ultrasound imaging. A processor is operable to convert ultrasound data in an acoustic coordinate format to display values in a Cartesian coordinate format. A display is operable to receive the display values and to display an image with the display values. The image is displayed without a raster buffer from conversion by the processor to display of the image by the display.

In a third aspect, a computer-readable medium has stored therein instructions executable by a processor for scan converting in ultrasound imaging. The instructions include generating a display image with video display color values, and calculating the video display color values from acoustic data. The calculating is at a rate synchronized with output of the video display color values to the display image where each of the video display color values is calculated as the video display color value is output to a pixel of the display image.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A display image is generated for a medical ultrasound machine. Video display color values are calculated in real time at the rate required by the display. The values are calculated for each of the image components, such as for B-mode, C-mode (i.e., color, flow, or Doppler), and overlay user interface graphics. Video signals may be generated without conversion of a complete raster image for storage and combination with overlay graphics. The video display color value for a pixel is calculated from the possible image components in real time at the rate at which data is provided to the display.

Figure 1:
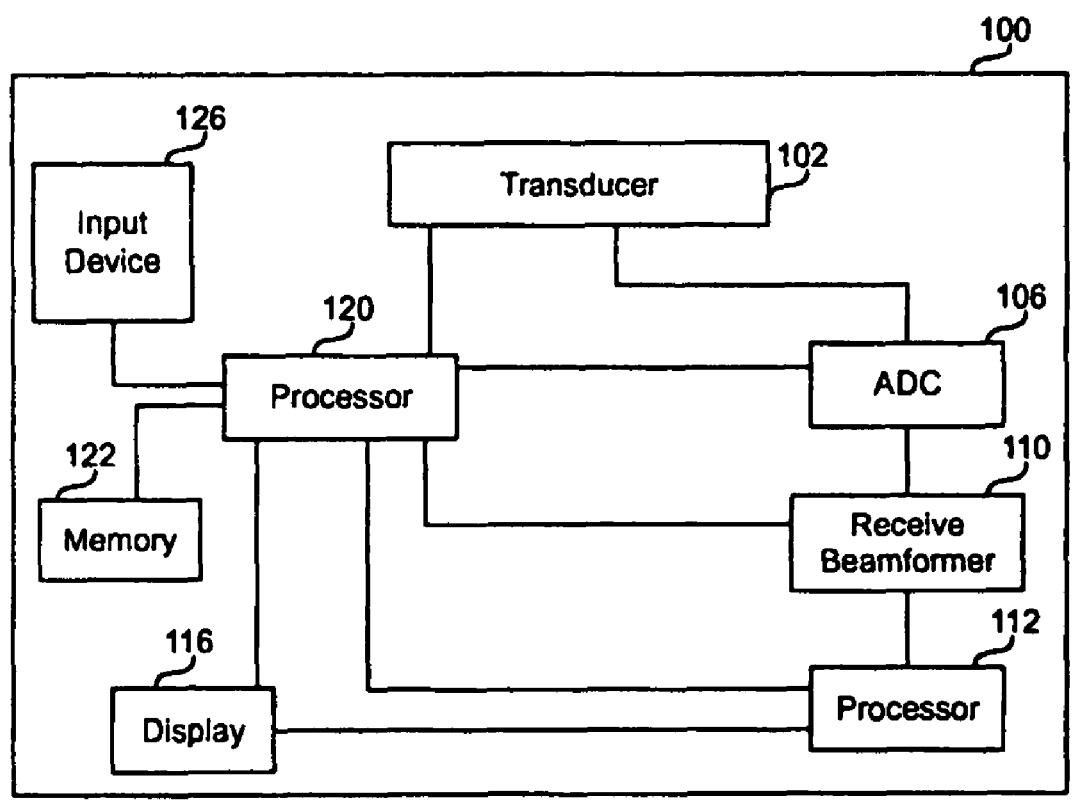
FIG. 1 is a block diagram of one embodiment of an imaging system for scan conversion.

FIG. 1 shows one embodiment of a medical diagnostic ultrasound imaging system 100. Any known or future dedicated ultrasound imaging system may be used. In other embodiments, the imaging system 100 may be a computer, a workstation, a server, and/or an image database system.

In one embodiment, the imaging system 100 is a cart based imaging system. In another embodiment, the imaging system 100 is a portable system, such as a briefcase-sized system or laptop computer based system. Other embodiments include handheld ultrasound systems. For example, one or more housings are provided where the entire system is small and light enough to be carried in one or both hands and/or worn by a user. The processors, transducer, display, and/or other components are provided in a single housing. In another example, a transducer is in one housing to be held by a person, and the imaging components and display are in another housing to be held by a person. Coaxial cables connect the two housings. As another example, the transducer and imaging components are in one housing and the display is in another housing hinged with the first housing. In any embodiment, the entire handheld system may weigh less than about 6 pounds, but may weigh more. For example, the handheld system weighs less than about 2 pounds, a weight around more commonly used medical equipment and more naturally born by medical professionals without burden. About allows for manufacturing tolerances.

The imaging system 100 performs scan conversion from an acquisition scan format to a display format. Coordinate conversion is provided. Conversion from ultrasound values to display values, such as red, green, blue values, is provided.

The imaging system 100 includes, but is not limited to, a transducer 102, an analog-to-digital converter ("ADC") 106, a receive beamformer 110, a processor 112, a display 116, an input device 126, a processor 120, and a memory 122. Additional, different, or fewer components may be provided. For example, probe electronics and a transmit beamformer are provided. In addition, the processor 112 and the processor 120 may be combined into one processor. The processor 112 may be separated into different components, such as one or more detectors and a scan converter. The ADC 106 may be a part of the receive beamformer 110. The input device 126 and/or the display 116 may be separate from but operable to communicate with the imaging system 100. Any or all of the electronics may be integrated in a single housing or few housings.

The imaging system 100, including the processor 112, is free of a raster buffer. Images are displayed without a raster buffer. For example, a raster buffer for storing display values for an entire image is not provided from scan conversion by the processor 112 to display of the image by the display. The entire image is the scan portion, but may also include background regions of the display screen. The image is displayed without storing display values for all pixels of the image. A buffer may be provided for a single display value, such as buffering 8, 16, or other bits for color components, such as for red, green, blue values for a pixel. Larger buffers may be used for storing values for a plurality of pixels, but fewer than for an entire image. For example, a shift register may be provided to shift a backlog of display values to pixels of the display. In other embodiments, a raster buffer for sufficient values for an entire image or more is provided.

The processor 120 connects with the memory 122, the display 116, the input device 126, the transducer 102, the ADC 106, the receive beamformer 110, and the processor 112. The processor 120 may connect with more or fewer components. The processor 120 is a main or control processor, such as a microprocessor, or a plurality of processors operable to control electronics of the imaging system 100.

The memory 122 is any known or future storage device. The memory 122 is a non-volatile and/or volatile memory, such as a Random Access Memory "RAM" (electronic), a Read-Only Memory "ROM" (electronic), or an Erasable Programmable Read-Only Memory (EPROM or Flash memory).

The input device 126 includes a button, a keyboard, a rocker, a joystick, a trackball, a voice recognition circuit, a mouse, and/or any other input device for sending commands in response to user activation. In one embodiment, the input device includes a trackball surrounding by buttons and a keyboard below the trackball and buttons.

The transducer 102 is a single transducer element, transducer array, or a plurality of transducer arrays. For example, the transducer 102 is a one dimensional linear phased or curved transducer array. In another example, the transducer is a multi-dimensional transducer array.

The transducer 102 includes one or more elements, such as 64 or 128 elements. Each element is a piezoelectric or microelectromechanical (e.g., capacitive membrane ultrasound transducer) transducer device, but other materials or structures may be used to convert between acoustical and electrical energies. For example, the transducer material is a multi-layered transducer material having at least two layers of piezoelectric ceramic transducer material. Alternatively, the transducer material is a semiconductor substrate with one or more flexible membranes (e.g., tens or hundreds for each element) formed within or on the semiconductor substrate. The transducer elements may also include any number of different layers, such as matching layers, flex circuit layers, signal traces, electrodes, a lens and/or a backing block.

The transducer 102, for example, is in an ultrasound probe connected with an ultrasound system or is in a housing for the entire system. The transducer 102 connects with the components of the system, such as connecting with the ADC 106, receive beamformer 110, and processor 112. The connections may be within a same housing or through one or more communication paths between housings (e.g., cables or wirelessly).

The transducer 102 is operable to receive acoustic signals and convert the acoustic signals into electrical energy. For example, the transducer 102 is operable to acquire ultrasound signals by receiving echo signals. The ultrasound signals include information for C-mode (e.g., Doppler mode, flow mode, velocity, energy, or variance), B-mode (grey-scale), and other tissue or flow information.

The ADC 106 receives signals from the transducer 102. The ADC 106 is a single or a plurality of any known or future analog-to-digital converters operable to sample analog signals, such as echo signals from tissue. For example, ADCs 106 connect with respective elements (channels) of the transducer 102. The elements connect directly to the ADCs 106. Alternatively, multiplexers provide for aperture control to connect elements to different channels at different times. To reduce a number of cables, the number of connections from the elements to the ADCs 106 may be reduced. Time multiplexing, frequency multiplexing, sub-array mixing, partial beamforming, or other processes for combining signals may be used. For example, signals from groups of four or other numbers of elements are combined onto common data paths by sub-array mixing, such as disclosed in U.S. Pat. No. 5,573,001 or U.S. Published Application No. 20040002652, the disclosures of which are incorporated herein by reference.

The receive beamformer 110 receives digital information for the elements or groups of elements from the ADC 106. Alternatively, the ADC 106 is incorporated into the receive beamformer 110. The receive beamformer 110 is an application specific integrated circuit ("ASIC"), processor, field programmable gate array ("FPGA"), analog components, digital components, integrated components, discrete devices, or combinations thereof. The receive beamformer 110 includes, but is not limited to, amplifiers, delay memories, a delay calculator, and channel adders for forming beams.

The receive beamformer 110 apodizes and relatively focuses the received samples. Electrical signals received from the transducer elements are relatively delayed and summed. Amplifiers may be provided for apodization. In one embodiment, the delays are implemented as memories for storing channel data (e.g., samples from each element). One or more memories may be used. For example, two memories or sets of memories operate in a ping-pong fashion to store data from elements and read data out for beamforming. Each memory or set stores element data for an entire scan. As one memory or set is storing, the other memory is outputting. By reading data out of the memory from selected memory locations, data associated with different amounts of delay is provided. The same data may be used for sequentially forming receive beams along different scan lines. Other memories may be used, such as a plurality of first-in, first-out buffers for delaying based on length and/or timing of input into the buffers.

The processor 112 receives beamformed ultrasound data from the receive beamformer 110. The processor 112 is a digital signal processor, graphics processing unit, main processor, microprocessor, field programmable gate array, application specific integrated circuit, video processor, graphics processor, analog circuit, digital circuit, or combinations thereof. The processor 112 is a single device or a plurality of processors. For example, the processor 112 is one central processing unit ("CPU"). Alternatively, the processor 112 is a plurality of devices in which each device is responsible for sampling and/or processing a portion of the data acquired by the imaging system 100.

In one embodiment, the processor 112 includes one or more detectors and/or filters. For example, a B-mode detector and a Doppler detector determine B-mode and C-mode ultrasound data. The B-mode ultrasound data represents the intensity of the received echo signals. The C-mode ultrasound data represents the motion or flow, such as velocity, power, and/or variance of fluid or tissue motion. For C-mode operation, a clutter filter may be provided to isolate information between tissues and fluid for C-mode estimation.

The processor 112 alternatively or additionally includes a scan converter. The same hardware operating under different code may implement the different operations of the processor 112. For example, coordinate and value conversions are implemented as hardware based state machines. Alternatively, different hardware of the processor 112 implements the different operations.

Scan conversion converts from a scan format to a display format, such as from a polar coordinate format of a sector or Vector® scan to a Cartesian coordinate format. A linear scan may be provided. Typically, the scan line density (azimuth) and/or sample density (range) is not equal to the display line density, so the acoustic data is converted for a linear scan. Other format conversions than polar to Cartesian may be used.

Figure 5:
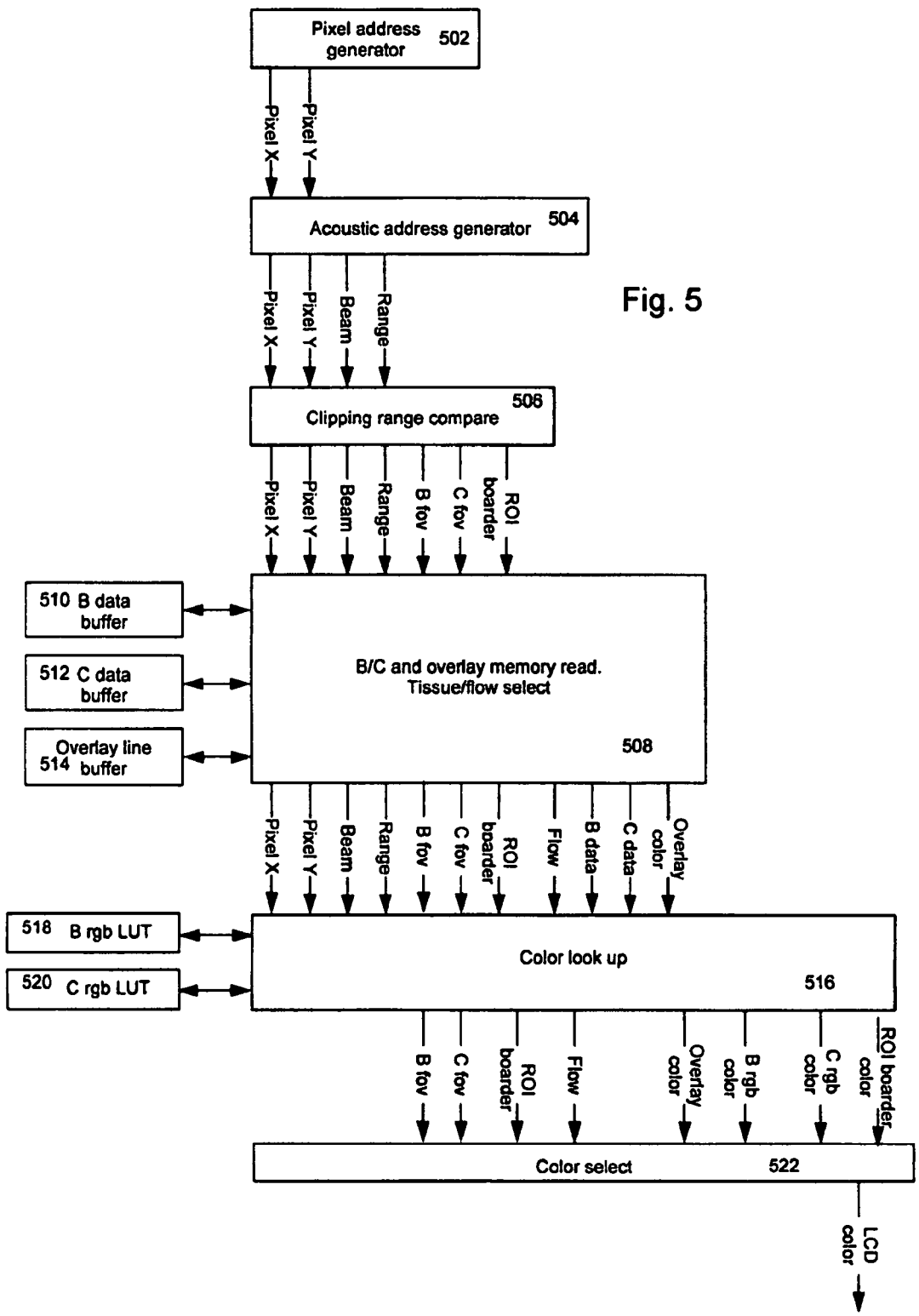
FIG. 5 is an example of a circuit or logic for scan conversion.

FIG. 5 represents a circuit, logic, or flow for scan conversion in one embodiment, but other embodiments without a pyramidal collection of data may be used. A display pixel location is converted to an acoustic scan location, or vise versa. For example, counters output X and Y pixel location values in order (line-by-line), as represented at 502. The count is changed sequentially for pipelined scan conversion. For conversion, a nearest acoustic location to a display pixel location is identified at 504. By selecting the ultrasound data at the identified acoustic data, the format is converted. As another example, four relative weights and corresponding acoustic locations surrounding a display pixel location are calculated and identified, respectively. The relative weights are a function of the relative distance of the identified acoustic locations to the display pixel location. The ultrasound data at the identified acoustic locations are weighted by the corresponding weight, combined, and normalized (interpolated) to convert the format. Other conversions may be used with or without interpolation. The scan conversion provides ultrasound data values for display pixel locations in the Cartesian coordinate or other display coordinate format.

The spatial extent of B-mode and C-mode data is determined for clipping at 506. The field of view of the B and C-mode data and any region of interest border are identified.

The scan conversion is provided for each type of ultrasound data. For example, B-mode ultrasound data is scan converted, and C-mode ultrasound data is scan converted. B-mode, C-mode, and any overlay data are provided from the buffers 510, 512, and 514, respectively. The same weights or interpolation may be applied to the different data to reduce calculations. Where the different types of ultrasound data are from different scan lines or scan distributions, entirely separate scan conversion may be used.

In one embodiment, the scan conversion is performed without pre-calculated look-up tables of weights or other interpolation information. The processor 112 interpolates based on the user selected scale, scan format (e.g., number of beams, spatial location of beams, depth, bounding box, and/or clipping), and/or image orientation relative to the desired screen space to be used for the image. Alternatively, one or more look-up tables are provided to assist or perform the scan conversion. The collection of data in the pipeline is read and selected data is output at 508.

The processor 112 is operable to assign display values as a function of the coordinate converted ultrasound data. For example, the processor 112 maps the ultrasound scalar values to color display values (red, green, blue (RGB); YUV; or other color format) using a look-up table 516. The weighting of the ultrasound data for coordinate conversion is performed for looking up the display color. The B-mode and C-mode data may use separate look-up tables 518, 520. Grey scale may be implemented by mapping the color components to equal or substantially similar levels (e.g., R=G=B). A function, look-up table, or other device or process may be used for mapping display values (e.g., RGB or YUV) from input ultrasound data (e.g., intensity and flow data).

The processor 112 is also operable to receive or generate a graphic overlay, such as data indicating border, text, region of interest, user interface, or other information to be displayed over or adjacent to the ultrasound data from the scan. In one embodiment, the processor 112 receives graphic overlay data from a video output of the processor 120, such as by direct memory access from a graphics buffer of the processor 120. The processor 120 determines the entire graphic overlay for each image and outputs or allows access to the graphic data.

Figure 2:
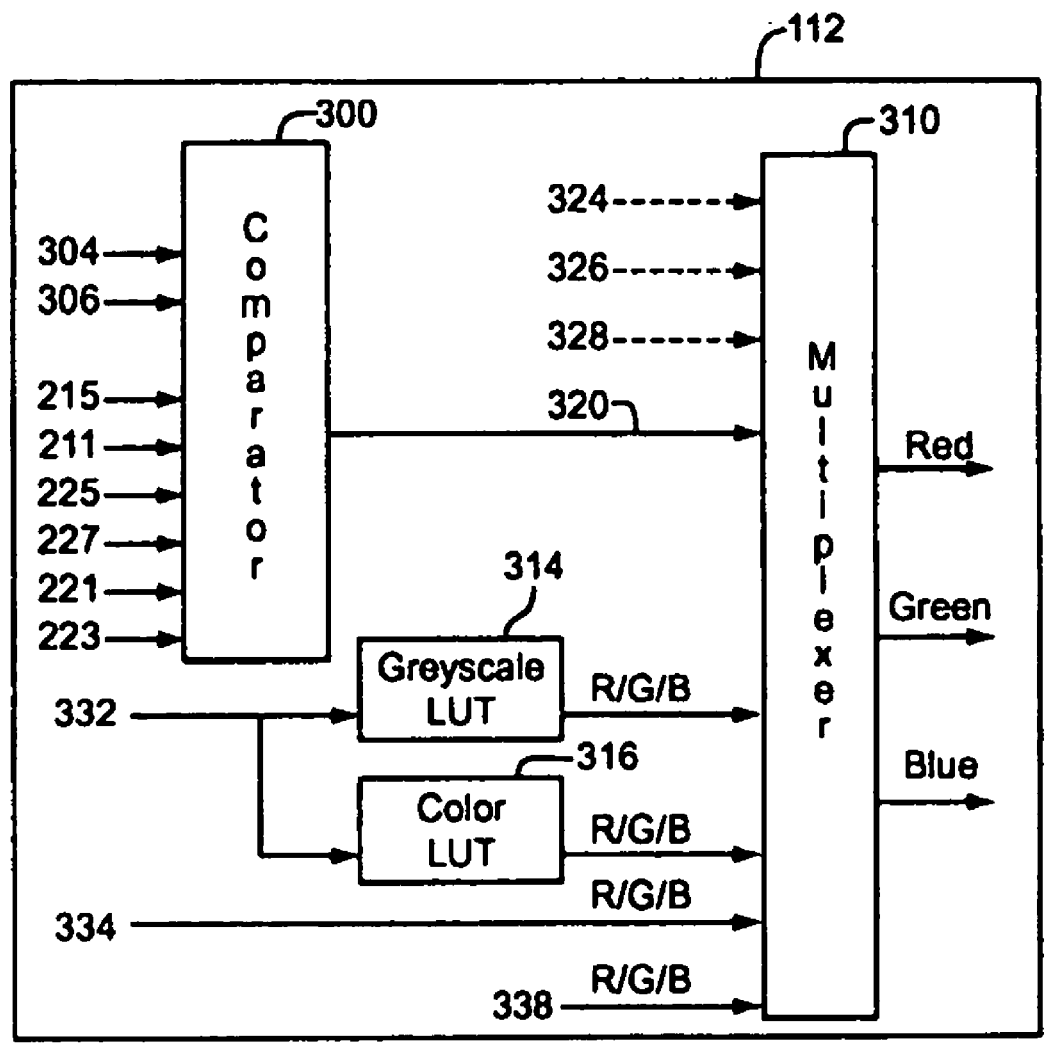
FIG. 2 is an example of a circuit or logic for scan conversion and calculating display values.

FIG. 2 is an example of a circuit within or process performed by the processor 112 for generating display values from input data, such as coordinate converted ultrasound data and graphic overlay data. For example, the processor 112 includes, but is not limited to, a comparator 300, a multiplexer 310 (the color select 522 of FIG. 5), a grey-scale look-up table ("LUT") 314, and a color LUT 316. Additional, different, or fewer operations or devices may be provided. In one embodiment, the specific devices shown are used in the processor 112. Alternatively, the processor 112 hardware is programmed with code to perform the operations represented by the blocks shown in FIG. 2.

The multiplexer 310 receives display values for the different types of data. The graphics overlay data is received from the processor in a display value format (e.g., RGB), but a look-up table or conversion process may be provided by the processor 112 in other embodiments.

The B-mode data is input to the look-up table 314. Using any desired mapping function, each B-mode ultrasound data value is converted to a display value, such as RGB components. True grey scale mapping may be used, such as all RGB components being equal. Tinting or intentional deviation from true grey scale may be provided to increase dynamic range.

The C-mode data is input to the look-up table 316. The color or C-mode look-up table 316 is separate from the grey scale or B-mode look-up table 314, such as being separate portions of a same memory or being separate memories. The graphics overlay data, C-mode data, and B-mode data may use independent color schemes. The color schemes may have different formats, such as number of bits.

Using any desired mapping function, each C-mode ultrasound data value is converted to a display value, such as RGB components. The mapping function is linear or non-linear. The mapping function may distinguish between directions, such as providing a shade of red for towards the array and a shade of blue for away from the array. Alternatively, the mapping function does not distinguish between directions, such as for mapping power information. Brighter colors may be used for larger or smaller C-mode values.

The processor 112 selects the B-mode display values, C-mode display values, or graphics overlay values for a given pixel in each image. The multiplexer 310 performs the selection based on output from the comparator 300. Alternatively, the selection is performed prior to coordinate scan conversion and/or prior to conversion to display values.

The assignment or allocation of a display value to a pixel is a function of prioritization of image information. For example, during each frame or multiple frames, each pixel is assigned video information. Depending on the screen dimensions of the display 116 or customization of image quality or dimensions, the processor 112, for example, assigns a Cartesian coordinate or other location information to each pixel. Then, based on the type of image to be generated as well as the selection of any region of interest, the appropriate text, border, tissue, and/or motion or flow RGB value is assigned to the pixel.

To determine which video information has priority, a predetermined chain of priority logic is used. The priority logic is stored on the memory 122, and/or multiplexer 310. For example, text information has priority over all other image data, and border information has the second highest priority. If a pixel corresponds to text, border, and tissue information, the text RGB value is allocated. Alternatively, if a pixel corresponds to only border and tissue information, the border RGB value is allocated. In another example, C-mode display values have priority over B-mode display values in a combined B/C-mode image.

The determination of what graphic overlay information corresponds to a respective pixel is implemented by comparator circuitry. For example, the comparator 300 is operable to determine whether at least one pixel of the plurality of pixels corresponds to a border. The comparator 300 receives pixel location values X and Y (304 and 306). The X and Y values 304 and 306 are defined as Cartesian coordinates or other location information for a pixel. The comparator 300 also receives the border dimensions or other graphic overlay location information to determine the locations of graphic overlay information. For example using a border, the comparator receive a range width 211, a beam width 215, a range minimum 221, a range maximum 223, a beam minimum 225, and a beam maximum 227 that defines the border. See U.S. Published application Ser. No. 20090018440 (application Ser. No. 11/827,679, filed Jul. 12, 2007), the disclosure of which is incorporated herein by reference, for one example embodiment using the same input reference numbers. The comparator is operable to compare the X and Y pixel location values 304 and 306 with the border dimensions to determine if the pixel is in or on a border area of the border of a region of interest. Other hardware or logic implementations than a comparator may be used, such as the processor 120 outputting the X and Y coordinates of the graphics overlay data.

The comparator 300 outputs a value 320 as a designation of whether a pixel corresponds to the text, border, or other graphics overlay feature or not. For example the value 320 is a flag bit that has a value "0" if the pixel being analyzed is not in or on a border area of the border and has a value "1" if the pixel is in or on the border area of the border. The value 320 is transmitted to the multiplexer 310.

Other flag bits represent whether the different types of information are available for a given pixel. Based on the coordinate conversion or other information, flags indicating available data are input to the multiplexer 310. For example, a text validation value 324, a tissue validation value 326, and a color validation value 328 are provided. If a pixel corresponds to text information, tissue information, or color information, then a "1" is used for the respective values, and a "0" is used if the pixel does not correspond to the respective information. Other flags, such as multi-bit flags, may be used.

The multiplexer 310 uses the validation values 320, 324, 326, 328, and 320 in conjunction with the predetermined chain of priority logic. Alternatively, a blending of two or more display values may occur. For example, the priority logic may allow both tissue information and border information to be allocated to the same pixel. The display values are averaged or otherwise combined, such as to allowing tissue to be viewed beneath a visible but relatively transparent border.

A display value is output for each respective pixel. After the multiplexer 310 receives the display values as well as the validation values, the multiplexer 310 outputs the appropriate display value to the appropriate pixel for each pixel in every frame or multiple frames.

The processor 112 outputs the display value for each pixel sequentially. Alternatively, groups of display values are output sequentially, such as associated with parallel processing. The processor 112 outputs the display values at a pixel rate. The display 116 is clocked to activate each pixel sequentially. Rather than wait for all display values before activating pixels for a same image, the processor 112 provides the display values as the pixel is to be activated.

Figure 3:
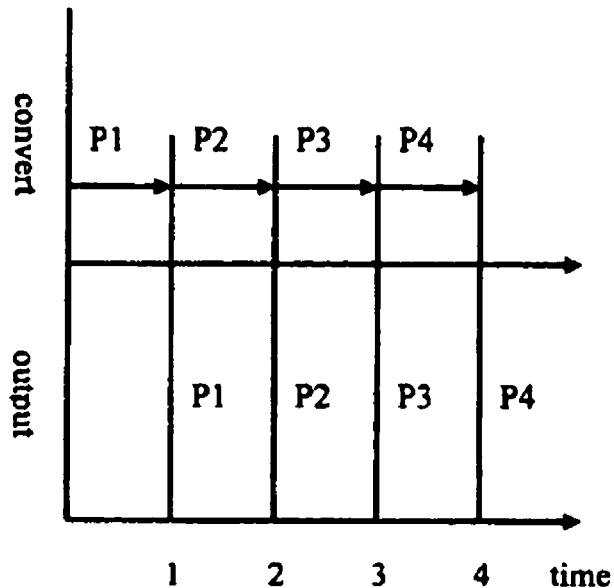
FIG. 3 is a timing diagram of one embodiment of scan converting and outputting display values to a display.

FIG. 3 shows one example. The display value for a first pixel (P1) is converted from ultrasound data. Once the conversion is complete, the display value is output on the display, activating a pixel, at time 1. Then, the display value for the next pixel (P2) is converted from ultrasound data. Once the conversion is complete, the display value is output on the display, activating the next pixel, at time 2. The process continues sequentially for each pixel on a line of the display, and then for the next line of the display to output an image. In other embodiments, pipeline processing may be used to begin processing the next conversion (e.g., coordinate conversion) prior to outputting the preceding conversion. The completion of conversion and output is still sequential. One or more pixel or group of pixel buffers may be provided between the completion of conversion and output to the display. Alternatively, direct output is provided without buffering.

The processor 112 operates in synchronization with the display 116. For example, the horizontal and/or vertical synchronization pulses of the display 116 are also used to time the clock and operation of the processor 112. The processor 112 is operated to output the display value for each pixel at a time when the display 116 is to receive the display value. The processor 112 operates as a state machine outputting display values and synchronization signals for the display 116.

Referring to FIG. 1, the display 116 receives display values (e.g., RGB) from the processor 112. The display 116 is any mechanical and/or electronic display. For example, the display 116 is a liquid crystal display ("LCD"), printer, or cathode ray tube ("CRT") monitor. Analog or digital displays may be used. The display 116 includes a plurality of pixels operable to show two dimensional ("2D"), three dimensional ("3D"), and/or four dimensional ("4D") images (i.e., the fourth dimension is time, and, therefore, 4D images are a sequence of images that show an object over a time period), such as ultrasound images. Each pixel includes a light source of a given color, such as red, green, and blue light sources. The relative intensity of the light sources at a pixel generates a particular color, brightness, hue, and shade for each given pixel.

The display 116 generates an image by sequentially providing pixel values by pixel within a line, line-by-line. For a next image, new display values are provided from a first pixel sequentially to a last pixel. The pixels may be maintained until changed or blanked prior to receiving the next value.

Figure 4:
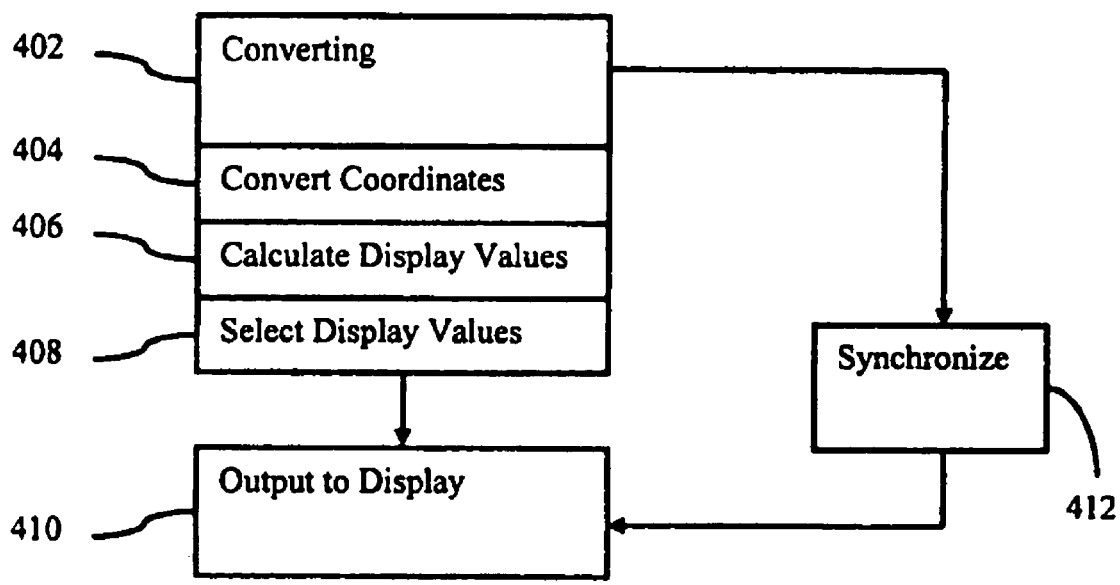
FIG. 4 is a flowchart of one embodiment of a method for scan converting.

FIG. 4 is a flowchart of one embodiment of a method of scan conversion in medical diagnostic ultrasound imaging. The method is implemented with the system 100 of FIG. 1, processor 112 of FIG. 2, or other scan converter. For example, the method is performed with a handheld ultrasound system weighing less than two pounds. The scan conversion is performed in one housing with a transducer, and display values are output to a hinge connected display. Other handheld or non-handheld ultrasound imaging systems may implement the method. The method is performed in the order shown or another order. Additional, different, or fewer acts may be performed. For example, act 404 is provided without acts 406 and 408 or vise versa.

Ultrasound data for generation of an image is acquired. For example, C-mode and/or B-mode data is acquired using a transducer. Graphics are also generated. Any data to be included on a given image is provided.

In act 402, data is converted to display or pixel values for output to a display. The data conversion includes coordinate or scan conversion (act 404) and/or conversion of value formats (act 406). Other conversions may be provided.

In act 404, the coordinate conversion is performed. The coordinate conversion alters the ultrasound data based on relative position between the scan format and the display format. For example, a display value address (pixel location) is provided. An acoustic coordinate is determined for a display value address. The ultrasound data associated with the acoustic coordinate is used to determine a scan converted ultrasound data value at the display value address. A nearest neighbor approach may be used. Alternatively, the scan converted ultrasound data value is interpolated from ultrasound data for a plurality of adjacent acoustic coordinates.

The scan conversion is performed for at least one type of data. In one embodiment, the scan conversion is performed for two or more types of data, such as B-mode and C-mode data. A data source is selected for the acoustic coordinate. The data source provides the ultrasound data to be scan converted.

For interpolation, the conversion is performed based on geometric relationships. The interpolation may be calculated as needed, such as free of look-up tables for coordinate conversion. Alternatively, look-up tables or other pre-calculation is performed to speed the coordinate conversion.

In act 406, for the display value address, display values are generated from a data source. The ultrasound data is converted to display values, such as RGB values. The scan or coordinate converted ultrasound data is used. For each display value address, display values are provided from the ultrasound data. Video display color values are calculated from acoustic data. For example, look-up tables or other linear or non-linear mapping associates the different possible ultrasound data values to display values.

The display values may be determined for B-mode and C-mode image components. For example, video display color values are calculated separately or independently from B-mode acoustic data, C-mode acoustic data, and graphics overlay data. The graphics overlay data may be provided in the display value format (e.g., RGB). In other embodiments, only one type of data is converted to display values.

In act 408, the display value (e.g., RGB values) for a given pixel is selected. Graphics overlay, B-mode, C-mode, or combinations thereof are selected. For selecting a combination, any combining function may be used, such as averaging or weighted averaging. The selection may be based on any desired criteria, such as overlay graphics being selected over other types of data, C-mode having a next priority, and B-mode having a lowest priority. Where overlay graphics are provided for a pixel location, the overlay graphics display value is selected. Where overlay graphics are not provided, a C-mode display value is selected unless not available, then a B-mode display value is selected. Other priority schemes may be used.

The display values or ultrasound data may be dithered to increase the dynamic range. Where the conversion of act 406 is independent for the types of data, separate dithering may be provided. The B-mode data may be dithered differently than C-mode data. One B-mode or C-mode data may not be dithered where the other is dithered. Both B-mode and C-mode data may be dithered in a same way. The graphics overlay data is not dithered. Dithering for graphics overlay is disabled by not providing the option to avoid artifacts. In other embodiments, the graphics overlay is dithered.

In act 412, the converting of act 402 is synchronized to a synchronization signal of the display. For example, the converting also generates the clocking and/or synchronization signals for driving the display. Pixel timing, line timing, and/or frame timing signals are output to the display in correspondence with the generation of the display values to be provided to the display. In alternative embodiments, the scan converting receives the synchronization signals from the display driver. The display values are generated in timing based on the received synchronization signals.

The display values are calculated at a rate synchronized with output of the video display color values to the display image. Each of the video display color values is calculated as output to a pixel of the display image. The conversion is performed as needed for output to the display. For example, each pixel value is scan converted and output prior to scan converting or completion of scan converting a subsequent pixel value for a same image. The converting is performed at a same rate as the outputting to the display.

In act 410, the pixel or display values are sequentially output to a display. A display image is generated with video display color values. As each pixel or display value is calculated, the value is used to operate the display at a corresponding pixel location. The pixel or display values are not stored in a memory together with the other values to be used to form the same image. Instead, red, green, and blue pixel values or other display values are output to the display as created and are created sequentially by pixel or groups of pixels.

Given a sufficiently high pixel rate, a sequence of images is displayed in substantially real time. For example, a frame rate of 30 Hz or better is provided by activating pixels sequentially.

The imaging system 100 includes instructions that can be executable by a processor, such as the processor 120 of FIG. 1, for scan conversion in ultrasound imaging. The instructions are stored in a computer-readable medium, such as the memory 122. The instructions implement the methods, acts, and processes described herein. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. In addition, any of the features, methods, techniques described may be mixed and matched to create different systems and methodologies.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system for scan conversion in medical diagnostic ultrasound imaging, the system comprising:
   a processor operable to convert ultrasound data in an acoustic coordinate format to display values in a Cartesian coordinate format, the processor being operable to convert the ultrasound data to the display values sequentially; and
   a display operable to receive the display values and to display an image with the display values, the image displayed without a raster buffer from conversion by the processor to display of the image by the display;
   wherein the processor and display are configured to activate each pixel of the display in sequence and prior to completion of the conversion of a next pixel to be activated in the sequence for the same image such that each pixel of the image is activated prior to the display value for the next pixel to be or being converted.

2. The system of claim 1 wherein the image is displayed without storing display values comprising all pixels of the image.

3. The system of claim 1 wherein the display values comprising red, green, blue values.

4. The system of claim 1 wherein the processor is operable to convert B-mode and C-mode ultrasound data, and wherein the processor comprises separate B-mode and C-mode look-up tables for associating the ultrasound values to red, green, and blue components of the display values, the processor operable to select the B-mode or C-mode display values for each pixel in the image.

5. The system of claim 1 further comprising a transducer connected with the processor, wherein the processor, the transducer, and the display are part of a handheld ultrasound system weighing less than about two pounds.

6. The system of claim 1 wherein the processor comprises a multiplexer, the multiplexer operable to select for at least one pixel of the display, the selection being from a group of graphic display values, B-mode display values, C-mode display values, and display values that are a combination thereof.

7. The system of claim 1 wherein the display comprises a digital liquid crystal display.

* * * * *